(12) United States Patent
Laufer et al.

(10) Patent No.: US 6,756,357 B1
(45) Date of Patent: Jun. 29, 2004

(54) VARIANTS OF HUMAN CILIARY NEUROTROPHIC FACTOR (HCNTF)

(75) Inventors: Ralph Laufer, Rome (IT); Annalise Di Marco, Rieti (IT)

(73) Assignee: Istituto di Richerche di Biologia Molecolare di Angeletti S.p.A., Pomezia (IT)

( * ) Notice: Subject to any disclaimer, the term of this patent is extended or adjusted under 35 U.S.C. 154(b) by 0 days.

(21) Appl. No.: 09/214,718

(22) PCT Filed: Jul. 10, 1997

(86) PCT No.: PCT/IT97/00163

§ 371 (c)(1),
(2), (4) Date: Jul. 6, 1999

(87) PCT Pub. No.: WO98/01149

PCT Pub. Date: Jan. 15, 1998

(30) Foreign Application Priority Data

Jul. 10, 1996 (IT) ........................................ RM96A0492

(51) Int. Cl.$^7$ ..................... C07K 14/475; A61K 38/18
(52) U.S. Cl. ..................... 514/12; 530/399; 930/120
(58) Field of Search .................... 530/399; 514/12; 930/120

(56) References Cited

U.S. PATENT DOCUMENTS 5,939,534 A * 8/1999 Inoue et al. ................. 530/399

FOREIGN PATENT DOCUMENTS

| WO | WO 94/09134 | 4/1994 |
| WO | WO 96/01319 | 1/1996 |

OTHER PUBLICATIONS

Jackowski: British J. Neurosurgery 9: 303–317, 1995.*
Rudinger, In "Peptide Hormones" (ed. J.A. Parsons) University Park Press, Baltimore, pp. 1–7, 1976.*
Barinaga Science 264: 772–774, 1994.*
Di Marco, Annalise et al., "Identification of ciliary neurotrophic factor (CNTF) residues essential for leukemia inhibitory factor receptor binding and generation of CNTF receptor antagonists.", Proc. Natl. Acad. Sci. USA., vol. 93, pp. 9247–9252 (1996).
Panayotatos, Nikos et al., "Exchange of a single amino acid interconverts the specific activity and gel mobility of human and rat ciliary neurotrophic factors.", The Journal of Biological Chemistry, vol. 268, No. 25, pp. 1900–19003 (1993).
Saggio, Isabella et al., "CNTF variants with increased biological potency and receptor selectivity define a functional site of receptor interaction.", The EMBO Journal, vol. 14, No. 13, pp. 3045–3054 (1995).

* cited by examiner

*Primary Examiner*—Gary Kunz
*Assistant Examiner*—Robert C. Hayes
(74) *Attorney, Agent, or Firm*—Sheldon O. Heber; Jack L. Tribble

(57) ABSTRACT

The variants of human ciliary neutrophic factor (hCNTF) according to the present invention are characterized by substitution of phenylalanine 152 and/or lysine 155 with alanine. These variants have biological properties that render them important as the active principles of drugs for the treatment of diseases and pathologies involving the nervous system or other pathologies involving cells responding to the CNTF. FIG. 2 shows the results of simulation of haptoglobin secretion from HepG2 cells by CNTF and the variants described in the invention.

5 Claims, 4 Drawing Sheets

VARIANTS OF HUMAN CILIARY NEUROTROPHIC FACTOR (HCNTF)

Figure 1A:
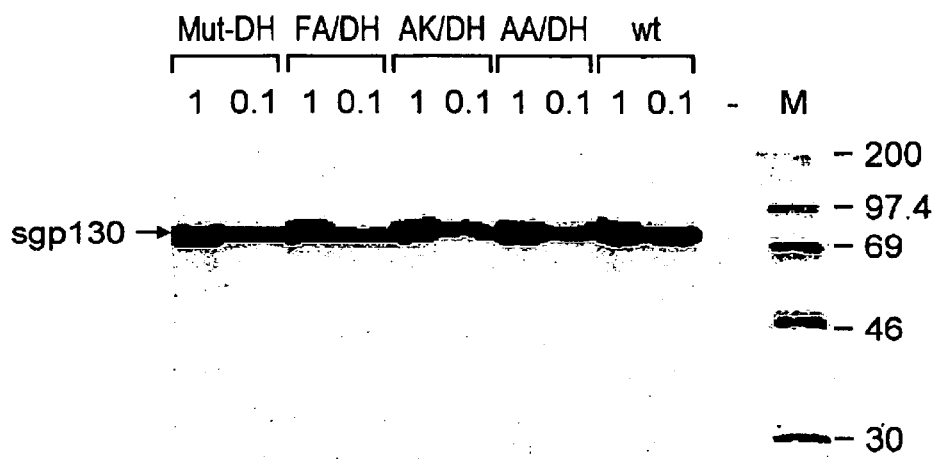

This application is the National Stage of International Application No. PCT/IT97/00163, filed Jul. 10, 1997.

FIELD OF THE INVENTION

The present invention relates to the field of neurology. Subject of the invention are mutants of the human ciliary neurotrophic factor (hCNTF) that show a range of action different from that of the wild-type molecule. These variants are characterised by the fact that they have a strongly reduced ability to interact with the LIF receptor (LIFR). As a consequence they have an extremely reduced biological activity on the majority of cells responding to CNTF. However, they retain a high biological activity on certain neurone cells, probably because the latter express large amounts of LIFR and/or CNTF receptor α (CNTFRα) bound to the membrane. This property can be used to reduce the peripheral side effects resulting from administration of CNTF.

BACKGROUND OF THE INVENTION

The human ciliary neurotrophic factor (hCNTF) is a neurocytokine of 23 kDa. It is expressed in Schwann cells and astrocytes, and exerts potent stimulatory effects on the survival and differentiation of a variety of neuronal and glial cells (both in vitro and in vivo), including motor neurons sensor neurons, sympathetic neurons, neurons of the hippocampus and oligodendrocytes (1, 2). The physiological role of CNTF would appear to be that of acting as a factor involved in the prevention of neuronal degeneration following injury (2). This protective action, which CNTF has shown in vivo on many nerve cells, has given hopes for its clinical application in the treatment of human neurodegenerative diseases (3).

As well as its neuroprotective action, however, it has been seen that CNTF also elicits in vivo a wide variety of effects, consisting of loss of weight and anorexia, acute-phase response and fever. There is therefore a problem with the pharmacological use of CNTF because of these side effects.

Like other growth factors, and in particular cytokines, CNTF exerts its actions through the binding, sequential assembly, and activation of a multisubunit receptor complex (4, 5). The receptor complex of which CNTF forms a part is made up of six subunits (similarly to the case of interleukin 6) (6). The complex is made up of two CNTF molecules, two α-receptor specific molecules forming a low-affinity bond with CNTF (CNTFRα) and two signal transducing subunits (LIFR and gp130) (11). The CNTF sites involved in binding with gp130 and with the specific receptor can be identified by analogy to interleukin 6 (7, 8, 10). The bonding site for CNTF and the LIF receptor (LIFR) has not yet been identified.

Multiple alignment of human, rabbit, rat and mouse CNTF sequences with other cytokine sequences that bind the LIF receptor (such as LIF, oncostatin M and CT-1) reveals the presence of two conserved amino residues within the structural motif known as D1. The two amino acids are phenylalanine in position 152 and lysine in position 155. As will be shown in greater detail in the following examples, the two amino acids form part of the LIFR bonding site. On the basis of this notion, CNTF mutants were generated in which the two amino acids were replaced by alanine, and the sequences of both the wild-type molecule (SEQ ID NO:1) and the mutants which are the object of the present invention are given in table 1 (for the sake of simplicity the whole amino acid sequence is not given, only the amino acid positions from 152 to 167). Although the literature indicates that one of the two mutants (Lys155Ala/CNTF) is completely inactive on hen neurons (10), the biological activity of both mutants was evaluated, and it was demonstrated that, contrary to previous reports (10), they act as powerful agonists on the membrane receptor of certain neuronal cells, whereas their biological activity is strongly reduced when they are bound to the LIF receptor or to the soluble CNTF receptor. A possible interpretation of this phenomenon may be the following: as the biological effects of these molecules depend on the concentrations of CNTFRα and LIF receptor, they are amplified when the local receptor concentration is very high, as is the case in receptors that are bound to the cell membrane of certain neuronal cell populations.

TABLE 1

| SEQ ID NO: | Amino acid |||||||||||||||| |
|---|---|---|---|---|---|---|---|---|---|---|---|---|---|---|---|---|---|
| | 152 | 153 | 154 | 155 | 156 | 157 | 158 | 159 | 160 | 161 | 162 | 163 | 164 | 165 | 166 | 167 | |
| 1 | Phe | Glu | Lys | Lys | Leu | Trp | Gly | Leu | Lys | Val | Leu | Gln | Glu | Leu | Ser | Gln | (hCNTF) |
| 2 | . | . | . | . | . | . | . | . | . | . | . | . | . | . | Asp | His | (MUT-DH) |
| 3 | Ala | . | . | . | . | . | . | . | . | . | . | . | . | . | Asp | His | (Phe152Ala/MUT-DH) |
| 4 | . | . | . | Ala | . | . | . | . | . | . | . | . | . | . | Asp | His | (Lys155Ala/MUT-DH) |
| 5 | Ala | . | . | Ala | . | . | . | . | . | . | . | . | . | . | . | . | (Phe152Ala/Lys155Ala/hCNTF) |
| 6 | . | . | . | Ala | . | . | . | . | . | . | . | . | . | . | . | . | (Lys155Ala/CNTF) |
| 7 | Ala | . | . | Ala | . | . | . | . | . | . | . | . | . | . | Asp | His | (Phe152Ala/Lys155Ala/MUT-DH) |

The discovery that these molecules exert a biological activity on neuronal cells expressing membrane-bound receptors and that on the contrary they show an extremely weak biological activity when interacting with the soluble receptor indicates that molecules that are modified in the positions indicated can be used for specific reaction with neuronal cells without causing peripheral side effects mediated by the soluble receptor bond.

Subject of the present invention are therefore variants of the human ciliary neurotrophic factor (hCNTF), characterised by replacement of the phenylalanine 152 and/or of the lysine 155 with alanine and comprising in particular an amino acid sequence chosen from the sequences indicated in SEQ ID NO:3 to SEQ ID NO:7.

The molecules represented by SEQ ID NO: 3 to SEQ ID NO:6 have a reduced ability to bond to the LIF receptor and to activate it by means of soluble CNTFRα, and on the contrary act as agonists on the CNTFR of certain neuronal cells. The molecule represented by SEQ ID NO:7 acts as a competitive antagonist for the CNTFRα receptor bond.

The present invention also extends to pharmaceutical preparations making use of these molecules for treatment of diseases or pathologies of the nervous system, or of other pathologies involving cells that respond to CNTF, including diseases or pathologies of the nervous system that cause damage to the nervous system itself.

Table 2 shows the data relating to CNTFRα receptor binding activities of the various mutants of CNTF. The concentration of protein needed to inhibit by 50% (IC50) the binding of biotinylated CNTF or biotinylated MUT-DH to immobilised CNTFRα was determined. Relative binding is the ratio (IC50 of CNTF)/(IC50 of tested protein).

TABLE 2

| Protein | Relative Binding |
| --- | --- |
| SEQ ID NO:1 | 1.0 |
| SEQ ID NO:2 | 41 ± 4 |
| SEQ ID NO:3 | 32 ± 11 |
| SEQ ID NO:4 | 42 ± 2 |
| SEQ ID NO:5 | 0.9 ± 0.1 |
| SEQ ID NO:6 | 1.0 ± 0.1 |
| SEQ ID NO:7 | 51 ± 19 |

Figure 1B:
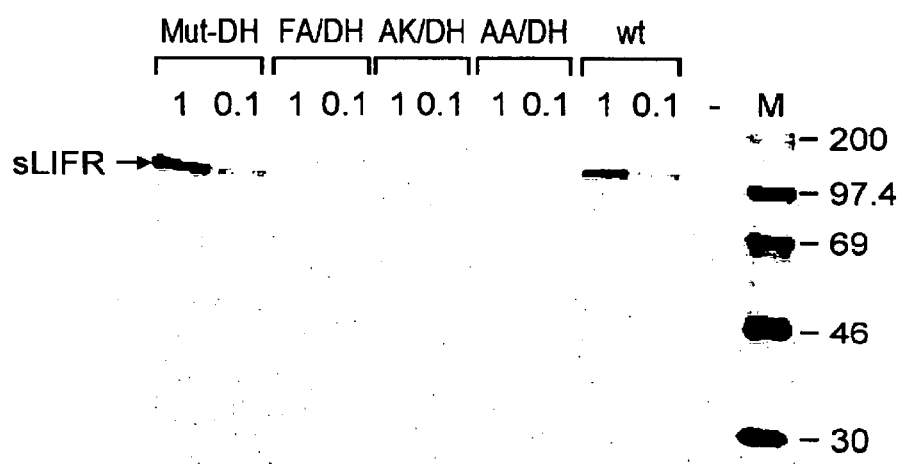
Figure 1C:
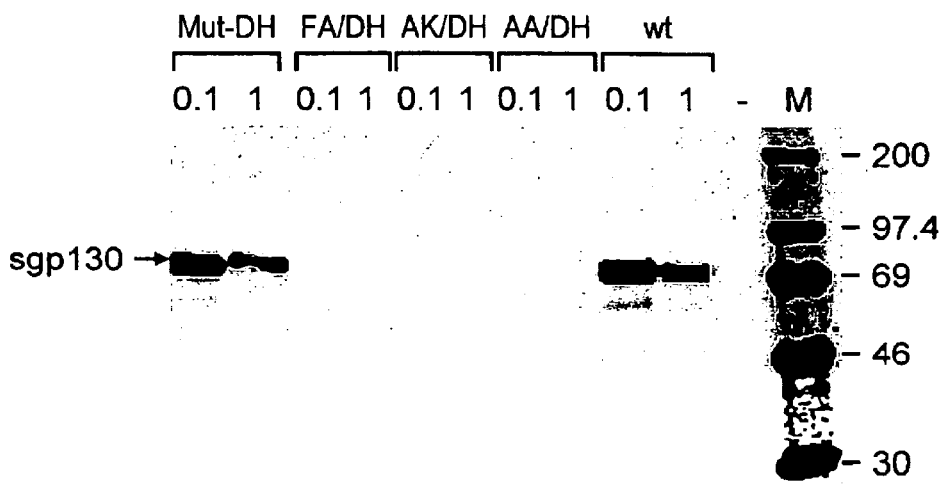

FIGS. 1A–C shows the results relating to binding tests on a number of receptor complexes, of which the variant CNTF molecules containing the subunits gp130 and LIFR form a part. Each test was carried out for two different amounts of variant molecules (1 or 0.1 mg, as indicated at the head of each column). In each figure the last column represents the negative control in which the test was carried out in the absence of variant molecules. (A) Binding test for the complexes containing the variants original MUT-DH, Phe152Ala/MUT-DH, Lys155Ala/MUT-DH, Phe152Ala/Lys155Ala/MUT-DH and wild-type CNTF (indicated as MUT-DH, AK/DH, FA/DH, AA/DH and wt, respectively) and CNTFRα with the receptor subunit gp130. (B) Binding test for the complexes containing the variants MUT-DH, Phe152Ala/MUT-DH, Lys155Ala/MUT-DH, Phe152Ala/Lys155Ala/MUT-DH and wild-type CNTF (indicated as MUT-DH, AK/DH, FA/DH, AA/DH and wt, respectively) and CNTFRα with the receptor subunit LIFR. (C) Binding test for the complexes containing the variants MUT-DH, Phe152Ala/MUT-DH, Lys155Ala/MUT-DH, Phe152Ala/Lys155Ala/MUT-DH and wild-type CNTF (indicated as MUT-DH, AK/DH, FA/DH, AA/DH and wt, respectively) and the complex LIFR/CNTFRα with the receptor subunit gp130.

Figure 2A:
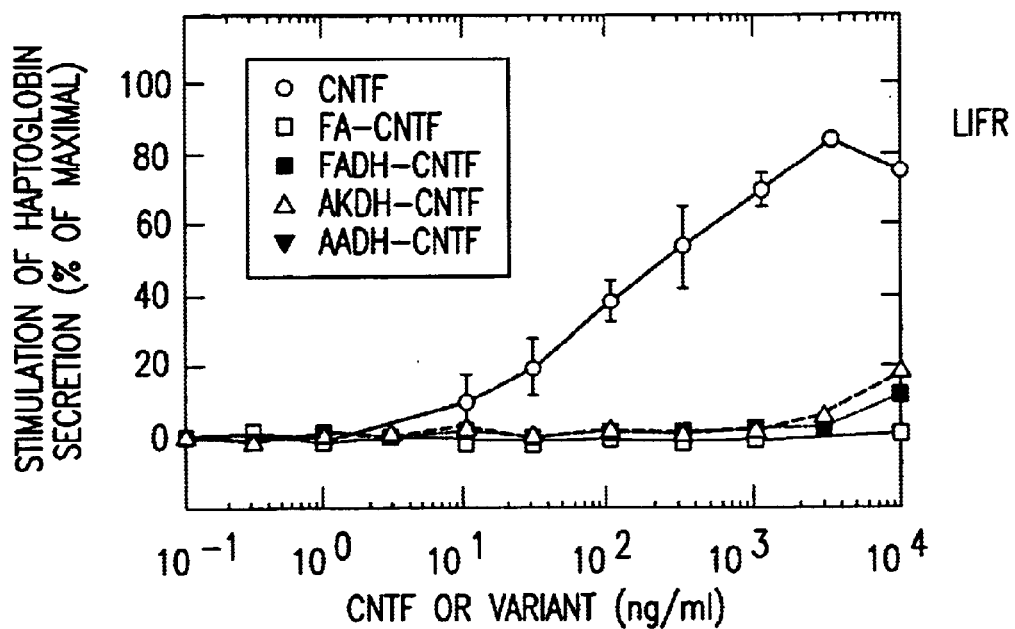
Figure 2B:
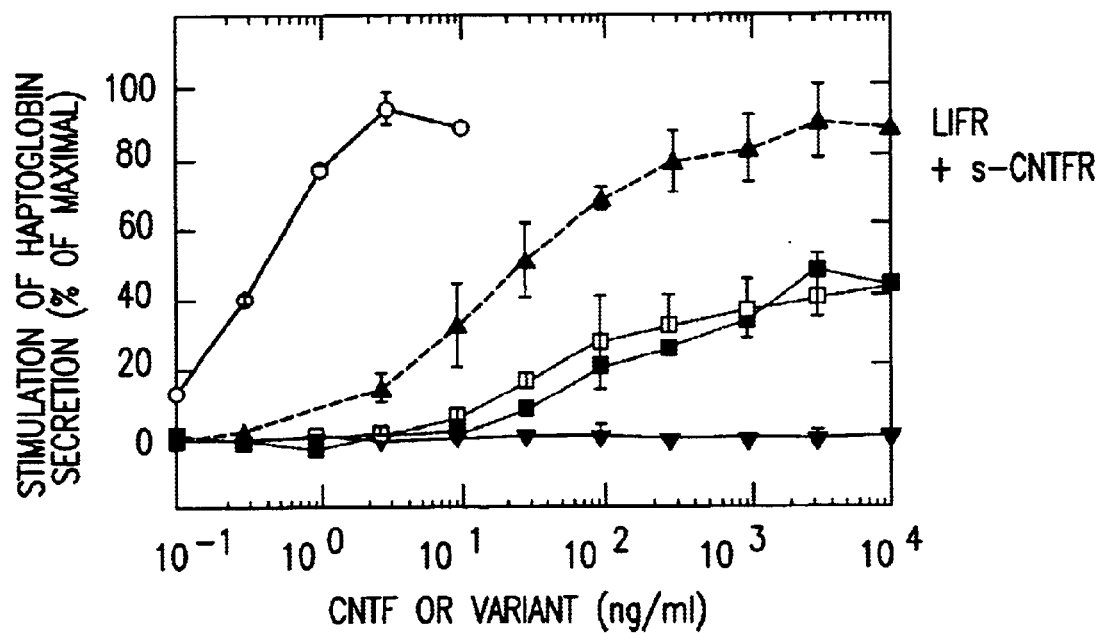

FIGS. 2A–B shows the results of stimulation of haptoglobin production in HepG2 cells by CNTF and CNTF variants. Experiments were performed either in the absence (A) or in the presence of soluble CNTFRα receptor at a concentration of 800 ng/ml (B). The proteins tested were: CNTF(O), Lys155Ala/CNTF (FA-CNTF)(□) Lys155Ala/MUT-DH (FADH-CNTF)(□), Phe152Ala/MUT-DH (AKDH-CNTF)(△) and Phe152Ala/Lys155Ala/MUT-DH (AADH-CNTF)(△). Data are expressed as a percentage of the maximal CNTF effect in order to normalise for differences between different experiments.

Figure 3:
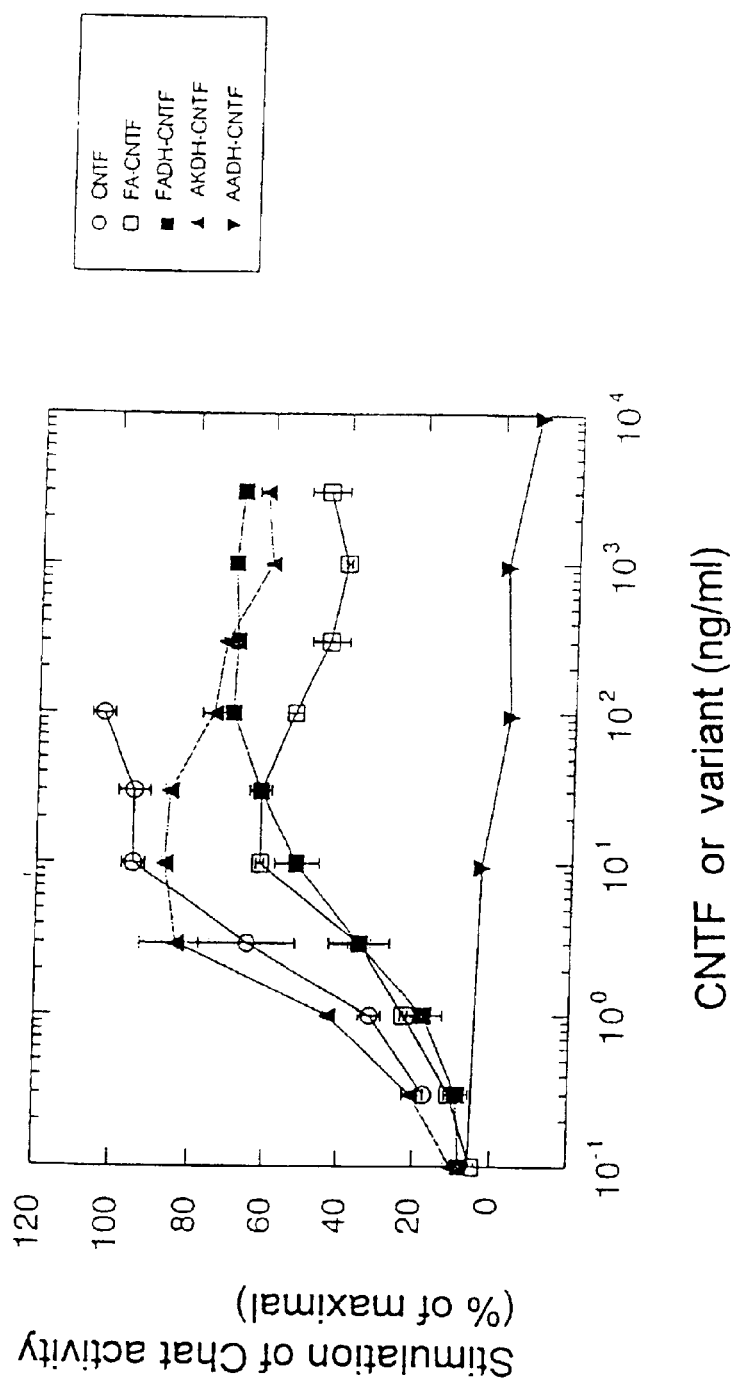

FIG. 3 shows the results of stimulation of choline acetyltransferase (Chat) activity in IMR-32 cells. The proteins tested were: CNTF(O), FA-CNTF(□), FADH-CNTF(□), AKDH-CNTF(▲)(n), and AKDH-CNTF(▼). Data are expressed as a percentage of the maximal CNTF effect in order to normalise for differences between different experiments.

Figure 4:
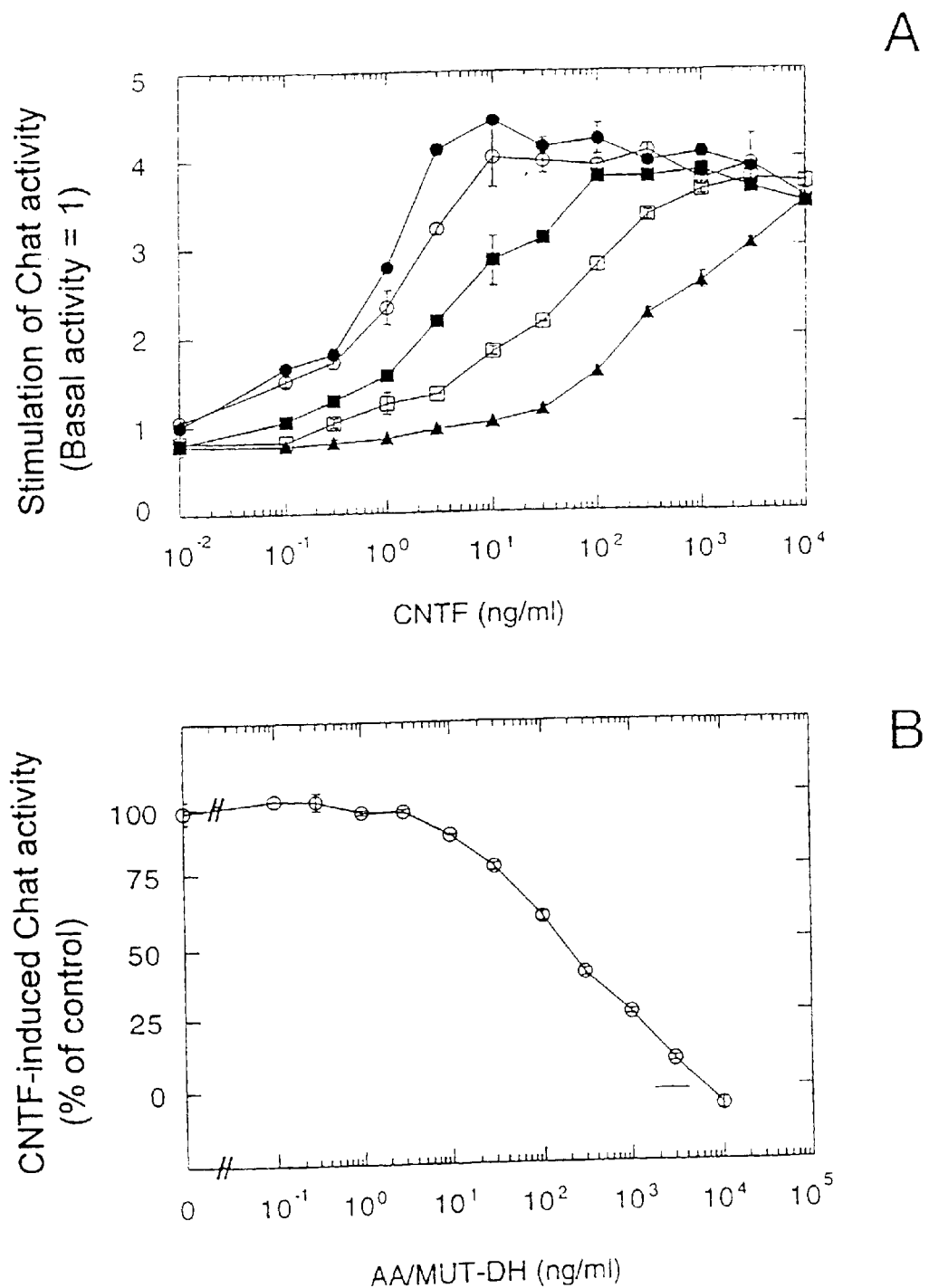

FIGS. 4A–B shows the antagonistic properties of the mutant Phe152Ala/Lys155Ala/MUT-DH in HepG2 cells. FIG. 4A shows the effect of increasing doses of CNTF on the choline acetyltransferase (Chat) activity in IMR-32 cells in the absence (O) and in the presence of the following concentrations of Phe152Ala/Lys155Ala/MUT-DH (in mg/ml): 0.01(O), 0.1(■), 1(□), 10(▲). FIG. 4B shows the effect of increasing concentrations of Phe152Ala/Lys155Ala/MUT-DH on the response induced by 3 ng/ml of CNTF.

So far a general description has been given of the present invention. With the aid of the following examples, a more detailed description of specific embodiments will now be given, in order to give a better understanding of the objects, characteristics, advantages and operating methods of the present invention.

DEPOSITS

*E. coli* TOP10 bacteria, transformed using the plasmids pRSET-AKDH-CNTF, pRSET-FADH-CNTF, pRSET-AADH-CNTF, respectively, containing the nucleotide sequences coding, respectively, for the variant AKDH-CNTF, which contains the amino acid sequence SEQ ID NO:3, for the variant FADH-CNTF, which contains the amino acid sequence SEQ ID NO:4, and for the variant AADH-CNTF, which contains the amino acid sequence SEQ ID NO:6, were filed on Jun. 24, 1996 with The National Collections of Industrial and Marine Bacteria Ltd. (NCIMB), Aberdeen, 5 Scotland, UK, with access numbers NCIMB 40809, NCIMB 40810 and NCIMB 40811.

EXAMPLE 1

Construction and Characterisation of CNTF Mutants Construction of Mutants

Mutations were introduced into the human CNTF or variant molecule MUT-DH (Ser166Asp/Gln167His/CNTF) by inverse PCR using a method known to the art (11), using the pRSET-CNTF or pRSET-MUT-DH vectors as templates. The following primers were used for PCR reactions: sense primer used for all mutants 5'-CTGTGGGGCCTAAAGGTGCTG-3' (SEQ ID NO:8) antisense primer for mutants Phe152Ala (the codon corresponding to Ala 152 is indicated in bold type) 5'-CGCCTTCTCAAAGAGACCACCATCTCCAAC-3' (SEQ ID NO:9) inverse primer for the mutants Phe152Ala/Lys155Ala (the codons corresponding to Ala 152 and Ala 155 are indicated in bold type) 5'-CGCCTTCTCAGCGAGACCACCATCTCCAAC-3' (SEQ ID NO:10)

The PCR reactions were performed using the DNA template (pRSET-CNTF or pRSET-MUT-DH; 10 fmol) and the primers (1 mM each) in 100 ml of reaction volume containing 2 units of Taq DNA polymerase (Boehringer Mannheim) and 10 ml of buffer for 10×PCR reaction. Amplification was carried out for 25 cycles of 1 minute at 94° C., 1 minute at 45° C. and 12 minutes at 72° C. The four deoxynucleotides (250 mM) and 20 units of *E. coli* polymerase I "Klenow fragment" were added to 95 ml of the amplified mixture, and the reaction mixture was incubated at 37° C. for 30 minutes. The DNA was isolated using the "Wizard™ PCR preps" purification system and phosphorylated by incubation with 20 units of T4 polynucleotide Kinase (Promega) in accordance with the manufacturer's instructions. The product was then run over agarose gel (0.7%) and then purified using a Qiaex kit (Qiagen), then made to undergo a ligase reaction using 12 units of T4 ligase at 16° C. for 20 hours. The reaction mixture was used to transform competent *E. coli* cells of the strain HB2151. The DNA was recovered from the bacteria cells and the identity of the regions coding for the CNTF mutants was established by sequencing the DNA using the USB Sequenase protocol.

The coding sequence for Phe152Ala/Lys155Ala/MUT-DH (AADH-PCR1) was found to contain two additional mutations (Ala70Thr/Val146Gly). To correct these mutations and return to the original sequence the following strategy was used: to eliminate the mutation Val146Gly an NcoI/PstI fragment comprising the coding sequence of CNTF from position 1 to position 163 was amplified using the DNA of AADH-PCR1 as a template, along with the following primers:

sense:
5'-GTCACCATGGCTTTCACAGAGCATTCACCG-3' (SEQ ID NO:11)

antisense: 5'-AGCTCCTGCAGCACCTTTAGGCCCCACAGCGCCTTCTCAGCGAGACCACCATCTCCAACATTAAT-3' (SEQ ID NO:12) (the codon for Val146 is indicated in bold type).

The PCR reaction was continued for 30 cycles (94° C. for 130 seconds; 50° C. for 130 seconds; 72° C. for 190 seconds) using 2.5 units of cloned pfu polymerase (Stratagene). The reaction product was digested with the enzymes NcoI and PstI, subjected to electrophoresis on 0.7% agarose gel and purified using the "Wizard™ PCR preps DNA" purification system (Promega). The fragment was then subcloned into the NcoI/PstI-digested pRSET-MUT-DH vector, thus obtaining the construct AADH-PCR2. To eliminate the mutation Ala70Thr, AADH-PCR2 DNA was digested with HindIII and the resulting fragment (which goes from the residue in position 79 to the residue in position 200 of the CNTF, and therefore excludes the mutation in position 70) was subcloned into a HindIII-digested pRSET-CNTF vector. The fact that the sequence actually codes for Phe152Ala/Lys155Ala/MUT-DH was confirmed by direct sequencing of the DNA sequence.

Expression of the protein and isolation of the bacterial inclusion bodies were achieved using the following procedure: the pRSET-CNTF and pREST-variant vectors were used to transform *E. coli* cells of the strain BL21 (DE3) LysE (SupE minus genotype). The transformants were stirred at 37° C. in 1 litre of Luria broth containing 0.1 mg/ml of ampicillin at an $A_{600}$ of 0.8. Subsequently, isopropylthiolgalactoside (0.4 mM) was added and incubation was continued for a further 3 hours at 37° C. The bacteria were then collected by centrifugation and resuspended in 2 ml per gram of beads in buffer A (100 mM Tris-Hcl, pH 7.5, 50 mM EDTA, 1 mM PMSF, 10 mg/ml leupeptin). To this was added 0.5 mg/ml of lysozyme and 30% w/v of sucrose. The suspension was incubated for 1 hour at 30° C. After the addition of one volume of buffer A, the bacteria were lysated by passing twice in succession through the "French Press" at a pressure of 800 bar. The inclusion bodies were isolated by centrifugation at 12000×g for 30 minutes. The beads were resuspended in a solution of 2 M guanidine chloride and were washed three times using the same solution, The final beads were resuspended in 5 ml of 8 M guanidine chloride solution and immediately diluted 4 times in buffer A. After centrifugation at 12000×g for 30 minutes the supernatant was dialysed at 4° C. against 10 mM Tris-HCl, 5 mM EDTA, 0.1 mM DTT pH 8 three times a decreasing concentrations of guanidine chloride (1 M, 0.5 M, 0 M, each time for one whole night) and once against 20 mM Tris, 0.1 mM EDTA, 1 mM DTT, 25 mM NaCl, pH 8. The final dialysed product was cleaned by centrifugation at 12000×g for 30 minutes and passed through a 0.22 mm filter. Subsequent purification was performed using by HPLC, using a C4 column (Vydac 214 TP, 2.2×25 cm, 10 mm) eluted at a flow rate of 30 ml/min. with a linear gradient of 40%–60% acetonitrile/0.1% trifluoroacetic acid in water/0.1% trifluoroacetic acid. Prior to removal of the solvent by lyophilization, 0.1% (w/v) n-octylglucopyranoside was added to the eluates. The protein was resuspended in water and stored at 4° C.

CNTFRα Receptor Binding Assay.

The ability of CNTF variants to compete with biotinylated CNTF (8 nM) for binding to the extracellular domain of the CNTFRα receptor was determined in a solid-phase binding assay, in the presence of soluble gp130, as described in preceding publications (19). "Microtiter" 96-well polystyrene culture plates were covered with 100 ml of 50 mM sodium carbonate pH 9.5, containing 0.2 mg of the monoclonal antibody 9E10, which is directed against a c-myc epitope, and the plates are then preserved at 4° C. for one night. The wells were then washed out five times with TBS (50 mM Tris-HCl, pH 7.5, 150 mM NaCl) containing 0.05% Tween and held for 90 minutes at room temperature in TBSMT (50 mM Tris-HCl, 150 mM NaCl, 5% (w/v) lyophilised non-fat milk). All subsequent incubations were carried out at room temperature on a mixer at a speed of 700 rpm, after each incubation period the wells were washed with TBS containing 0.05% Tween (five times each time). The following incubation periods were performed: (1) 2 hours with 50 ml TBSMT containing 10 mg of CNTFRα-myc; (2) 1 hour with 50 ml of TBSMT containing 200 ng of gp130-flag, 5 nM biotinylated CNTF, and the various competitors and (3) 45 minutes with 50 ml of TBS, 5% (w/v) of bovine serum albumin, 0.05% (v/v) Tween 20 containing 0.8 mg/ml avidin conjugated with alkaline phosphatase.

The alkaline phosphatase activity was determined at 37° C. using 1 mg/ml p-nitrophenyl phosphate in 1 M of diethanolamine-HCl, pH 9.8, and absorbancy at 405 nm was measured after 40–60 minutes using a suitable reader. In some experiments the biotinylated MUT-DH variant molecule (0.5 nM) as used as a ligand.

The competition assay showed that substitution of the residues Phe152 and Lys155 with alanine did not modify the interaction with the CNTFRα receptor. The two mutants Lys155Ala/CNTF and Phe152Ala/Lys155Ala/CNTF were equipotent with the wild-type molecule in binding to the receptor. As previously reported (18), the molecule MUT-DH is approximately 40 times more powerful than CNTF in receptor binding. In this case also the mutants Phe152Ala/MUT-DH, Lys155Ala/MUT-DH and Phe152Ala/Lys155Ala/MUT-DH were equipotent with the original molecule (MUT-DH) in binding to the receptor. These results, which are summarised for greater clarity in table 2, demonstrate that the residues Phe152 and Lys155 do not participate in binding to the CNTFRα receptor.

Assembly of the Receptor Complex in vitro.

It is known from the literature that the molecules gp130 and LIFR are able to bind independently to the CNTF/CNTFRα complex (11). To assess the functional importance of D1 motif residues the ability of CNTF variants to assemble receptor complexes with the different subunits was assayed. Bonding of the cytokine/CNTFRα complex to gp130 or LIFR marked with $^{35}S$ was determined using immunoprecipitation tests as described in the literature (11). The soluble CNTFRα receptor was immobilised on A-Sepharose protein using the monoclonal antibody 9E10 anti-myc and incubated with soluble gp130 or LIFR marked with sulphur $^{35}S$, in the absence or in the presence of different amounts of CNTF variants (1 or 0.1 mg). After washing, the bound material was eluted and subjected to SDS-PAGE.

As shown in FIG. 1A, gp130 binding to the complex MUT-DH/CNTFRα is not influenced by the substitutions Phe152A (column AK/DH), Lys155A (column FA/DH) and Phe152A/Lys155A (column AA/DH). In contrast, as seen from FIG. 1B, variants bearing these substitutions either singly or together were unable to bind to the LIFR receptor. To test the ability of the variants to form the tripartite CNTFRα/gp130/LIFR complex, the LIFR receptor was immobilised on the protein A-Sepharose and incubated with soluble CNTFRα, soluble gp130 marked with $^{35}S$ and with the CNTF variants (in this case also the experiment was performed twice on two different amounts of the variant molecules, 1 or 0.1 mg).

In line with the first two results the variant molecules were unable to bind to the CNTFRα/gp130/LIFR complex, which corresponds to the physiologically active form of the CNTF receptor on the cell surface (see FIG. 1C).

These results show that Phe152 and Lys155 form part of the LIFR receptor binding site.

EXAMPLE 2

Biological Activity of CNTF Mutants
Assay on the Secretion of Haptoclobin by Human Hepatoma Cells.

Biological activity was determined in cell-based assays capable of measuring the ability of CNTF (or the mutants) to assemble a functional receptor complex between soluble CNTFRα and cellular LIF receptors. The human hepatoma cell line HepG2 does not express CNTFRα, whereas it does express the LIF receptor and responds only to high concentrations of the cytokine, probably because of a low-affinity interaction of CNTF with cellular LIF receptors (18, 13). The assay was carried out as follows. First of all, the HepG2 cells were grown in 96-well plates until they formed a confluent single layer, then they were placed in a minimum culture medium containing 1 mM dexamethasone (14) and were treated for 24 hours with purified CNTF or with the variant molecules being tested. The amount of haptoglobin secreted by the cells in the culture medium was determined using an ELISA test.

As haptoglobin secretion is mediated by the LIFR cellular receptor it is supposed that amino acid substitutions that impair binding to this receptor will lead to a strong reduction in biological activity of this type when compared to the wild-type molecule. In effect, if substitution of Phe152 or Lys155 by alanine gives a weak biological activity (approximately 20% with respect to the maximum value) at high concentrations, simultaneous substitution of both residues with alanine completely abolishes biological activity, even at high concentrations (FIG. 2A). In the presence of soluble CNTFRα, cells bearing LIFR and gp130 receptors become sensitive to low concentrations of CNTF, due to the formation of the complete receptor complex. As can be seen from FIG. 2B the increase in the concentration of exogenous CNTFRα leads to a shift of the cellular response towards lower concentrations of CNTF and its variants.

Moving on the analysis of the behaviour of single variants, it can be said that the mutants Lys155Ala/CNTF (FA-CNTF) and Lys155Ala/MUT-DH (FADH-CNTF) have a biological activity that is strongly reduced but not totally abolished. On the other hand the alanine substitution of the residue Phe152 (AKDH-CNTF) reduces the molecule's biological activity to a lesser extent than substitution of the residue Lys155 and simultaneous substitution of both residues (AADH-CNTF) totally abolishes this activity, even at high concentrations of both receptor and cytokine.

Stimulation of Choline Acetyltransferase (Chat) Activity in IMR-32 Cells.

To determine the effects of the variants on the membrane-bound CNTF neuron receptor, the molecules were tested for their ability to stimulate that activity in human neuroblastoma cells (IMR-32) using methods known from the literature (15, 22). These cells constitutively express the CNTFRα receptor. The IMR-32 membrane-bound receptors were found to be less sensitive than the soluble receptor to the effect of the single mutations in positions 152 and 155. The mutant Phe152Ala/MUT-DH was as active as the wild-type cytokine, and the variants Lys155Ala/CNTF and Lys155Ala/MUT-DH actually showed themselves to be powerful agonists. However, in this case also the simultaneous substitution of the two residues results in a total loss of biological activity.

The high biological activity of the mutants Phe152Ala and Lys155Ala in IMR-32 cells is probably due to the high local concentration of receptor subunits on the surface of the cell. Actually, it is to be expected that CNTF mutants with a reduced LIFR receptor binding capacity will continue to maintain a strong stimulating activity on other neuronal populations expressing high levels of membrane receptor complexes, as for example those participating in motor functions. It is believed that the side-effects resulting from administration of CNTF, for example acute-phase response, are mediated by the action that the circulating soluble CNTFRα receptor exerts on the cells expressing the LIFR receptor (for example hepatocytes). It is therefore expected that CNTF mutants which show weak activity when interacting with the soluble receptor and on the contrary show a high level of biological activity when interaction is with the cell's membrane-bound receptor complexes, have a more specifically neuronal action, reducing peripheral side-effects.

EXAMPLE 3

Antagonist Properties of Certain CNTF Variants

It is expected that CNTF mutants that have lost the ability to bind to the LIF receptor but are still able to assemble CNTFRα and gp130 will act as competitive antagonists. Inhibition of the biological activity of CNTF by these mutants was tested in IMR-32 cells using the procedure described in Example 2. The variant protein Phe152Ala/Lys155Ala/MUT-DH caused a shift of the CNTF response curve towards high concentrations of the agonist molecule, demonstrating that it acts as a competitive antagonist on membrane-bound CNTFRα receptor. A 50% inhibition of Chat activity induced by a subsaturating dose of CNTF was obtained with a 70-fold excess of Phe152Ala/Lys155Ala/MUT-DH (FIG. 4B). EXAMPLE 4

Construction of CNTF Variants

Mutations were introduced into the human CNTF or S166D/Q167H/CNTF (DH-CNTF) sequences by inverse PCR (Hemsley et al., 1989), using the pRSET-CNTF or PRSET-MUT-DH vectors (Italian patent application RM9500380) as templates. Synthetic oligonucleotide primers were constructed to lie "back to back" on the duplex, with 5' ends apposing and 3' ends oriented for extension in opposite orientations around the plasmid circle. The primers used were:

antisense primer for FA-CNTF and FADH-CNTF:
5'CGCCTTCTCAAAGAGCCACCATCTCCAAC3' (SEQ ID NO:13)
antisense primer for AKDH-CNTF:
5'CTTCTTCTCAGCGAGACCACCATCTCCAAC3' (SEQ ID NO:14)
antisense primer for AA-CNTF and AADH-CNTF:
5'CGCCTTCTCAGCGAGACCACCATCTCCAAC3' (SEQ ID NO:10)

These mutant primers were used in PCR together with the sense wild-type primer:
5'CTGTGGGGCCTAAAGGTGCTG3' (SEQ ID NO:8)

Template DNA (10 fmol), and primer sets (1 mM each) were incubated in 100 ml of reaction volume containing 100 mM Tris-HCl pH 8.3, 500 mM KCl, 15 mM $MgCl_2$, 0.2 mM of each dNTP and 2 nits of Taq polymerase (Boehringer).

The amplification proceeded through a cycle of denaturation at 94° C. (1 min), annealing at 45° C. (1 min) and primer extension at 72° C. (12 min) for a total of 25 cycles. Five microliter portions of the sample generated by PCR were analysed on an agarose gel (0.7%) to determine the efficiency of the amplification. The remainder (95 ml) was treated with Klenow fragment of E. coli polymerase I (20 units) and the four dNTP at the final concentration of 250 mM each. The reaction mix was incubated at 37° C. for 30 min. Double strand DNA was isolated from the PCR reaction mixtures using Wizard PCR preps DNA purification system (Promega) and phosphorylated at the 5' end by incubation with 20 units of T4 polynucleotide Kinase (Promega) and 1 mM ATP.

The phosphorylated DNA samples were then subjected to electrophoresis on agarose gels (0.7%), and the appropriate bands were excised and purified using a Qiagen DNA purification kit. A volume of 10 microliter of DNA (out of 25 ml total) was used in a ligase reaction containing standard blunt-end ligation buffer and T4 DNA ligase (12 units). The ligation mixes were incubated overnight at 16° C., and then heated to 65° C. and used to transform competent E. coli Top 10 cells. Transformants were isolated and the identity of the clones was confirmed by DNA sequence analysis.

The coding sequences for AA-CNTF and AADH-CNTF were found to contain 2 additional mutations (probably due to PCR-induced errors) at nucleotides 208 and 435. The latter mutation was eliminated by PCR using the following sense and antisense primers:

sense:
5 1'GTCACCATGGCTTTCACAGAGCAT-TCACCG3' (SEQ ID NO:11)
antisense:
5'AGCTCCTGCAGCACCTTTAGGCCCCA-CAGCGCCTTCTCAGCGAGACCAC-CATCTCCAACATTAAT3' (SEQ ID NO:12)

PCR was performed for 30 cycles of 140 sec at 94° C., 140 sec at 50° C., and 190 sec at 72° C. using 2.5 U of pfu DNA polymerase (Stratagene), according to the manufacturer's instructions. PCR products were isolated as described above, digested with NcoI (site located at nucleotide -2 of the CNTF coding sequence) and PstI (site at nucleotide 484 of the coding sequence) and subcloned into the NcoI/PstI- digested pRSET-CNTF or pRSET-DH-CNTF vectors. This procedure gave rise to vectors containing the coding sequence for AA-CNTF or AADH-CNTF, with a remaining mutation at nucleotide 208. This mutation was eliminated by digestion of the vectors with HindIII (site located at nucleotide 233 and at the end of the coding sequence), and replacement of the large restriction fragment (comprising nucleotides 1 to 233) with the corresponding fragment from pRSET-CNTF.

BIBLIOGRAPHY

1. Manthorpe M., Louis J. C., Hagg T. & Varon S. (1993) in Neurotrophic factors, eds Loughlin S. E. & Fallon J. H. (Academic Press, Dan Diego, Calif.), pages 443–473.
2. Sendtner M., Carrol P., Holtmann B., Hughes R. A. & Thoenen H. (1994) J. Neurobiol. 25:1436–1453.
3. Lindsay R. M., Wiegand S. J., Altar C. A. & Di Stefano P. S. (1994) Trends Neurosci. 17:182–190.
4. Stahl N. & Yancopoulos G. D. (1994) J. Neurobiol. 25:1454–1466
5. Kishimoto T., Akira S., Narazaki M. & Taga T. (1995) Blood 86:1243–1254.
6. Fuh G., Cunningham B. C., Fukunaga R., Nagata S., Goeddel D. V. & Wells J. A. (1992) Science 256:1677–1680.
7. Savino R., Lahm A., Salvati A. L., Ciapponi L., Sporeno E., Altamura S., Paonessa G., Toniatti C. & Ciliberto G. (1994) EMBO J. 13:1357–1367.
8. Brakenhoff J. P. L., de Hon F. D., Fontaine V., Boekel E. T., Schooltingk H., Rose-John S., Heinrich P. C., Content J. & Aarden L. A. (1994) J. Biol. Chem. 269:86–93.
9. Hudson K. R., Vernallis A. B. & Heath J. K. (1996) J. Biol. Chem. in press.
10. Inoue M., Nakayama C., Kikuchi K., Kimura T., Ishige Y., Ito A., Kanaoka M., and Noguchi H. (1995); Proc. Natl. Aca. Scie. USA, 92: 8579–8583.
11. De Serio A., Graziani R., Laufer R., Ciliberto G. & Paonessa G. (1995) J.Mol.Biol. 254:795–800.
12. Savino R., Lahm A., Giorgio M., Cabibbo A., Tramontano A. & Ciliberto G. (1993) Proc. Natl. Acad. Sci. USA 90:4067–4071.
13. Savino R., Ciapponi L., Lahm A., Demartis A., Cabibbo A., Toniatti C., Delmastro P., Altamura S. & Ciliberto G. (1994) EMBO J. 13: 5863–5870.
14. Robinson R. C., Grey L. M., Staunton D., Vankelekom H., Vernallis A. B., Moreau J. F., Stuart D. I., Heath J. K. & Jones E. Y. (1994) Cell 77:1101–1116.
15. Bazan E. (1991) Neuron 7:197–208.
16. Hemsley A., Arnheim N., Toney M. D., Cortopassi G. & Galas D. J. (1989) Nucl. Acids Res. 17:6545–6551.
17. Masiakowsky P., Liu H., Radziejewsky C., Lottspeich F., Oberthuer W., Wong V., Lindsay R. M., Furth M. E. & Panayotatos N. (1991) J. Neurochem. 57:1003–1012.
18. Saggio I., Gloaguen I., Poiana G. & Laufer R. (1995) EMBO J. 14: 3045–3054.
19. Saggio I., Paonessa G., Graziani R., Di Serio A & Laufer R. (1994) Anal. Biochem. 221:387–391.
20. Baumann H., Ziegler S. F., Mosley B., Morella K. K., Pajovic S. & Gearing D. P. (1993) J. Biol. Chem. 268:8414–8417.
21. Baumann H., Ziegler S. F., Mosley B., Morella K. K., Pajovic S. & Gearing D. P. (1993) J. Biol. Chem. 268:8414–8417
22. Saggio I., Gloaguen I. & Laufer R. (1995) Gene 152:35–39.
23. Rabinovsky E. D., Browder D. P., & McManaman J. L. (1994) J. Neurosci. Res. 38:127–133.

What is claimed is:

1. A variant of human ciliary neurotrophic factor (hCNTF) in which amino acid residues numbers 152 to 167 as depicted as SEQ ID NO: 1 are replaced by SEQ ID NO:3 or SEQ ID NO:4.

2. The variant of hCNTF of claim 1, wherein amino acid residues numbers 152 to 167 as depicted in SEQ ID NO: 1 are replaced by SEQ ID NO: 3.

3. The variant of hCNTF of claim 1, wherein amino acid residues numbers 152 to 167 as depicted in SEQ ID NO: 1 are replaced by SEQ ID NO: 4.

4. A composition comprising at least one of the variants of hCNTF according to claim 1 in a carrier, vehicle, or auxiliary agent.

5. The composition according to claim 4 wherein the carrier, vehicle, or auxiliary agent is pharmaceutically acceptable.

* * * * *

SEQUENCE LISTING

<160> NUMBER OF SEQ ID NOS: 14

<210> SEQ ID NO 1
<211> LENGTH: 16
<212> TYPE: PRT
<213> ORGANISM: Artificial Sequence
<220> FEATURE:
<223> OTHER INFORMATION: sequence for human CNTF from position 152 to position 167

<400> SEQUENCE: 1

Phe Glu Lys Lys Leu Trp Gly Leu Lys Val Leu Gln Glu Leu Ser Gln
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: sequence of human CNTF from position 152 to position 167 containing Ser166Asp/Gln167His

<400> SEQUENCE: 2

Phe Glu Lys Lys Leu Trp Gly Leu Lys Val Leu Gln Glu Leu Asp His
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: sequence of human CNTF from position 152 to position 167 containing Phe152Ala/Ser166Asp/Gln167His

<400> SEQUENCE: 3

Ala Glu Lys Lys Leu Trp Gly Leu Lys Val Leu Gln Glu Leu Asp His
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: sequence of human CNTF from position 152 to position 167 containing Lys155Ala/Ser166Asp/Gln167His

<400> SEQUENCE: 4

Phe Glu Lys Ala Leu Trp Gly Leu Lys Val Leu Gln Glu Leu Asp His
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: sequence of human CNTF from position 152 to position 167 containing Phe152Ala/Lys155Ala

<400> SEQUENCE: 5

Ala Glu Lys Ala Leu Trp Gly Leu Lys Val Leu Gln Glu Leu Ser Gln
1               5                   10                  15

<210> SEQ ID NO 6
<211> LENGTH: 16

```
<212> TYPE: PRT
<213> ORGANISM: Artificial Sequence
<220> FEATURE:
<223> OTHER INFORMATION: sequence of human CNTF from position 152 to
      position 167 containing Lys155Ala

<400> SEQUENCE: 6

Phe Glu Lys Ala Leu Trp Gly Leu Lys Val Leu Gln Glu Leu Ser Gln
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: sequence of human CNTF from position 152 to
      position 167 containing
      Phe152Ala/Lys155Ala/Ser166Asp/Gln167His

<400> SEQUENCE: 7

Ala Glu Lys Ala Leu Trp Gly Leu Lys Val Leu Gln Glu Leu Asp His
 1               5                  10                  15

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ctgtggggcc taaaggtgct g                                            21

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
cgccttctca aagagaccac catctccaac                                   30

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
cgccttctca gcgagaccac catctccaac                                   30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
gtcaccatgg ctttcacaga gcattcaccg                                   30

<210> SEQ ID NO 12
<211> LENGTH: 65
<212> TYPE: DNA
<213> ORGANISM: Artificial Sequence
```

```
-continued

<220> FEATURE:
<223> OTHER INFORMATION: Primer

<400> SEQUENCE: 12
agctcctgca gcacctttag gccccacagc gccttctcag cgagaccacc atctccaaca      60
ttaat                                                                 65

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
cgccttctca aagagccacc atctccaac                                       29

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
cttcttctca gcgagaccac catctccaac                                      30
```